(12) United States Patent
Parhi et al.

(10) Patent No.: US 7,642,279 B2
(45) Date of Patent: Jan. 5, 2010

(54) ATIPAMEZOLE HYDROCHLORIDE CRYSTALLIZATION METHOD

(75) Inventors: Seppo Parhi, Oulu (FI); Arto Karjalainen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 11/913,776

(22) PCT Filed: Jun. 16, 2006

(86) PCT No.: PCT/FI2006/000210

§ 371 (c)(1),
(2), (4) Date: Jan. 3, 2008

(87) PCT Pub. No.: WO2006/134219

PCT Pub. Date: Dec. 21, 2006

(65) Prior Publication Data

US 2008/0275252 A1 Nov. 6, 2008

(30) Foreign Application Priority Data

Jun. 17, 2005 (FI) .................................. 20050657

(51) Int. Cl.
*A01N 43/50* (2006.01)
*C07D 233/00* (2006.01)
(52) U.S. Cl. .................................. 514/396; 548/335.1

(58) Field of Classification Search .............. 548/335.1; 514/396

See application file for complete search history.

(56) References Cited

U.S. PATENT DOCUMENTS 4,689,339 A * 8/1987 Karjalainen et al. ......... 514/396

OTHER PUBLICATIONS

Atherton, J. H. et al "Process Development: Physicochemical Concepts," XP002407479, Oxford University Press, Oxford (1999) pp. 9-11.*
Atherton, J. H. et al "Process Development: Physicochemical Concepts," XP002407479, Oxford University Press, Oxford (1999) pp. 9-11.
International Search Report dated Nov. 27, 2006, for International Application No. PCT/FI2006/00210.
Written Opinion for International Application No. PCT/FI2006/00210, dated Nov. 27, 2006.

* cited by examiner

*Primary Examiner*—Golam M. M. Shameem
*Assistant Examiner*—Susannah Chung
(74) *Attorney, Agent, or Firm*—Finnegan, Henderson, Farabow, Garrett & Dunner, L.L.P.

(57) ABSTRACT

A method of isolating atipamezole hydrochloride as a crystalline salt is provided.

11 Claims, No Drawings

ATIPAMEZOLE HYDROCHLORIDE CRYSTALLIZATION METHOD

This application is a national stage filing under 35 U.S.C. 371 of International Application No. PCT/FI2006/000210, filed on Jun. 16, 2006, which claims the benefit of priority of Finnish Application No. 20050657, filed on Jun. 17, 2005. The contents of each application are incorporated herein by reference.

FIELD OF THE INVENTION

The present invention relates to a method of preparing atipamezole hydrochloride. Particularly the present invention relates to an improved method of isolating atipamezole hydrochloride as crystalline salt.

BACKGROUND OF THE INVENTION

Atipamezole which is 4-(2-ethyl-2,3-dihydro-1H-inden-2-yl)-1H-imidazole of formula I

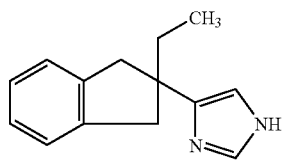

is a well known pharmaceutical agent currently used as its hydrochloride salt in reversal of the effects of sedative-analgesic veterinary drugs.

The preparation of atipamezole hydrochloride salt is described in U.S. Pat. No. 4,689,339, wherein atipamezole obtained from the hydrogenation step is first recovered from alkaline solution as free base. After the evaporation of methylene chloride solvent to dryness the isolated crystalline product is converted into its hydrochloride salt by treatment with dry hydrogen chloride in ethyl acetate.

SUMMARY OF THE INVENTION

The present invention is directed to an improved method of isolating atipamezole hydrochloride salt. The novel method is more efficient and economical than the method previously disclosed. In particular, the method of the present invention provides crystalline atipamezole hydrochloride directly without the need to isolate atipamezole base. Furthermore, the use of methylene chloride and ethyl acetate solvents is avoided, as crystalline atipamezole hydrochloride can be obtained directly from its water solution.

DETAILED DESCRIPTION OF THE INVENTION

The present invention provides a method for preparing atipamezole hydro-chloride wherein the method comprises a) hydrogenation of compound of formula (II) or a salt thereof

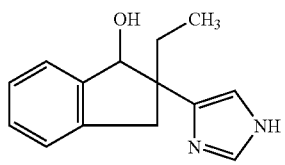

in aqueous solution of hydrochloric acid under catalyst;
b) concentrating the solution by distillation;
c) cooling the concentrated solution; and
d) recovering crystallized atipamezole hydrochloride.

The hydrogenation of the compound of formula (II) is suitably performed in aqueous solution comprising hydrochloric acid. The amount of hydrochloric acid is suitably from about 1 to about 20%, preferably from about 5 to about 15%, for example from about 8 to about 12%, per total weight of the aqueous solution.

The weight ratio of compound (II) to the solvent of aqueous solution is preferably from about 1:5 to about 1:30, more preferably from about 1:8 to about 1:25, for example from about 1:14 to about 1:20.

Preferably, at least about 50%, more preferably at least about 55%, suitably at least about 60%, per weight of the solvent of aqueous solution is water.

Advantageously, the aqueous solution contains from about 1 to about 50%, preferably from about 5 to about 45%, more preferably from about 10 to about 40%, for example from about 15 to about 35, per weight of lower alcohol, preferably ethanol.

Suitably the hydrogenation is performed in the presence of a catalyst under hydrogen atmosphere at normal or elevated hydrogen pressure. Suitable catalysts include palladium, platinum, Raney-nickel and platinum oxide. Palladium or platinum is conveniently used on a carrier such as charcoal. Palladium-on-charcoal is the preferred catalyst. Reaction is conducted at normal or elevated temperature, for example at 25-100° C., preferably at 60-80° C., for a period until the hydrogenation reaction is finished. Typical reaction time is about 10-20 hours. After the hydrogenation, the mixture is preferably cooled and filtered.

In the next step the aqueous filtrate solution containing atipamezole is concentrated. This is performed suitably by distilling off part of the solvent under reduced pressure. This is performed suitably by distilling off part of the aqueous solvent under reduced pressure at boiling temperature. Preferably, the solution is concentrated by distilling off from about 30 to about 70% per weight, more preferably from about 35 to about 65% per weight, for example from about 45 to 60% per weight, of the total amount of solvent present in the solution.

If necessary, hydrochloric acid may be added to the concentrated solution to obtain the desired hydrochloric acid concentration for crystallizing atipamezole hydrochloride upon cooling of the solution. Preferably, the concentrated solution from which the crystallization is carried out comprises from about 5% to about 35%, more preferably from about 10% to about 30%, for example from about 15% to about 25%, per weight of hydrochloric acid.

The crystallization of atipamezole hydrochloride is suitably carried out by cooling the solution to a temperature which is lower than 20° C., preferably lower than 15° C., more preferably lower than 10° C., and especially lower than 5° C. It is particularly preferred to carry out crystallization by cooling the solution to a temperature which is from about −5° C. to about 5° C., for example from about −2° C. to about 2° C.

The cooling is preferably carried out during 0.5 to 10 hours, typically during 1 to 3 hours, for example during 2 hours. The solution is preferably agitated in the crystallization temperature, preferably from 0.5 to 5 hours, typically from 1 to 3 hours. If desired, the solution can be seeded with atipamezole hydrochloride crystals during the cooling process until the crystallization starts. This can be performed stepwise at various temperatures during cooling, e.g. by adding seeding crystals at 100° C., 90° C., 80° C. and 70° C., until the crystallizations starts.

The crystalline product can be recovered from the solution by conventional methods such as centrifugation or filtering. The crystalline product can be washed with suitable solvent and dried at elevated temperature. Suitably, the wet product is dried in vacuum at about 35-90° C. for 20-50 hours.

If desired, the product can be recrystallized by repeating the above crystallization step, e.g. by dissolving the product into water by warming, distilling off part of the water solvent, adding hydrochloric acid, cooling and recovering the recrystallized product.

The following example is used to illustrate but by no means to limit the scope of the invention, which is defined in the claims.

Example 1

Preparation of 4-(2-ethyl-2,3-dihydro-1H-inden-2-yl)-1H-imidazole hydrochloride (atipamezole HCl)

4-(2-ethyl-2,3-dihydro-1-hydroxy-1H-inden-2-yl)-1H-imidazole (5 kg), water (40 kg), 30% HCl (34 kg), ethanol (22 kg) and 10% palladium on charcoal (0.5 kg) are charged. The mixture is stirred under 2.2 bar overpressure of hydrogen at 80±3° C. for 12 hours. The reaction mixture is filtered at 73±2° C., the filter cake is washed with water (7 kg) and the filtrates are combined. The reaction mixture is heated to boil and 50 l of the solvent is distilled off. The solution is cooled to 0±2° C. during 2 h. The solution is seeded during the cooling procedure with atipamezole HCl at 100±5° C., 90±5° C., 80±5° C. and at 70±5° C., until the crystallization starts. The mixture is agitated for two hours at 0±2° C. The crystalline compound is recovered by centrifugation and washed with HCl-water mixture (0.34 kg HCl and 10 kg of water) and then with 18 kg of acetone. The product is dried under reduced pressure raising the temperature gradually to 85±3° C. The yield is 4.8 kg (89%).

The invention claimed is:

1. A method for preparing atipamezole hydrochloride comprising:

a) hydrogenation of a compound of formula (II):

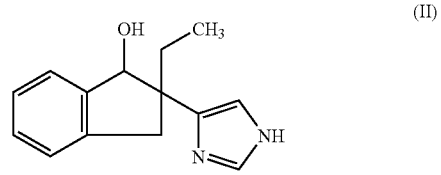

, or a salt thereof,
  in an aqueous solution of hydrochloric acid performed in the presence of a catalyst, wherein the aqueous solution comprises from 10% to about 40% per weight of a lower alcohol;
b) concentrating the aqueous solution by distilling off from about 30% to about 70% per weight of the total amount of the aqueous solution;
c) cooling the concentrated solution; and
d) recovering crystallized atipamezole hydrochloride, wherein the concentrated solution from which the crystallization is carried out comprises from about 10% to about 30% per weight of hydrochloric acid.

2. The method according to claim 1, wherein at least about 50% per weight of the aqueous solution is water.

3. The method according to claim 2, wherein at least about 55% per weight of the aqueous solution is water.

4. The method according to claim 1, wherein the lower alcohol is ethanol.

5. The method according to claim 1, wherein the weight ratio of compound (II) to the aqueous solution is from about 1:5 to about 1:30.

6. The method according to claim 5, wherein the weight ratio of compound (II) to the aqueous solution is from about 1:8 to about 1:25.

7. The method according to claim 1, wherein the solution is concentrated by distilling off from about 35% to about 65% per weight of the total amount of the aqueous solution.

8. The method according to claim 1, wherein the concentrated solution is cooled to a temperature less than 10° C.

9. The method according to claim 8, wherein the concentrated solution is cooled to a temperature which is from about −5° C. to about 5° C.

10. The method according to claim 1, wherein the cooling in step c) is carried out for from 0.5 to 10 hours.

11. The method according to claim 10, wherein the cooling in step c) is carried out for from 1 to 3 hours.

* * * * *